United States Patent [19]

D'Angelo et al.

[11] Patent Number: 5,443,080
[45] Date of Patent: Aug. 22, 1995

[54] INTEGRATED SYSTEM FOR BIOLOGICAL FLUID CONSTITUENT ANALYSIS

[75] Inventors: Joseph P. D'Angelo; Henry Schur; Kedu Han, all of Miami; Daniel J. Glenn, Hollywood, all of Fla.

[73] Assignee: Americate Transtech, Inc., Miami, Fla.

[21] Appl. No.: 173,635

[22] Filed: Dec. 22, 1993

[51] Int. Cl.⁶ .............................................. A61B 5/00
[52] U.S. Cl. ................................. 128/771; 128/760; 128/766; 128/632
[58] Field of Search ............... 128/637, 760, 766, 771, 128/632, 636; 424/449

[56] References Cited

U.S. PATENT DOCUMENTS

| | | | |
|---|---|---|---|
| 2,292,450 | 8/1942 | Kohn | 128/760 X |
| 4,595,011 | 6/1986 | Phillips | 128/760 X |
| 4,821,733 | 4/1989 | Peck | 128/766 X |
| 4,846,182 | 7/1989 | Fogt et al. | 128/760 X |
| 4,957,108 | 9/1990 | Schoendorfer et al. | 128/760 X |

FOREIGN PATENT DOCUMENTS 964072  7/1964  United Kingdom ............... 128/637

Primary Examiner—Sam Rimell
Attorney, Agent, or Firm—Herbert L. Lerner; Laurence A. Greenberg

[57] ABSTRACT

A multi-part system to collect and analyze constituents of body fluid. The use of a multilayered gel matrix to facilitate the collection of analytes fluid and a chemistry detection methodology incorporated into the matrix to aid in the visual or electronic determination of the analyte is described.

12 Claims, 10 Drawing Sheets

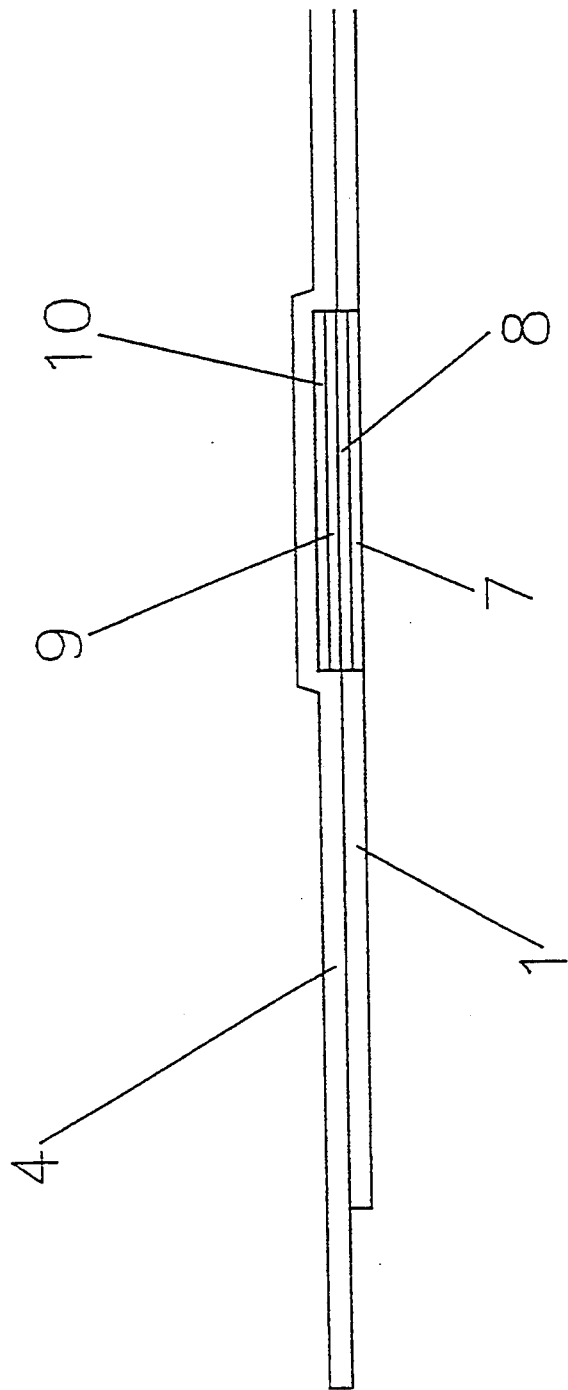

INTEGRATED SYSTEM FOR BIOLOGICAL FLUID CONSTITUENT ANALYSIS

BACKGROUND OF THE INVENTION

1. Field of the Invention

The invention relates to monitoring a medical condition by collecting, detecting and interpreting biological fluids.

2. Description of the Related Art

Biological fluids are currently collected by a variety of means, including venipuncture, saliva, sweat, and urine, to name a few of the most common. After collection the sample is usually processed or otherwise treated in order for a chemical test to be performed. In some cases the sample can be analyzed directly using modern dip-stick technology or elaborate and complicated clinical laboratory instruments.

Errors occur frequently in the processing or handling of the sample which then requires additional sampling, time delays, and reduced patient care.

The problems associated with obtaining a sufficient amount of sample required to test on commonly used methodologies is magnified even further when the sample source is a small animal or infant.

The advent of home testing devices for conditions such as diabetes and pregnancy have stressed the importance of sample collection and the immediacy of results as well as the intimacy of the testing.

Current technology is at a state of development wherein 1) a sample can be collected via a distasteful or painful method and 2) the collected sample is then separately tested for the desired component if the quantity and/or quality of the sample is correct.

From the above, it is clearly seen that it would be a significant advancement in the art if an integrated system for accomplishing both the sample collection and test in the form of a simple to use device could be provided. Some of the features required from such a system include improved accuracy of the test results, removal of undesireable and extra steps from the procedures (reducing error and incovenience), and, in the case of repetitive testing, removing the inconvenience and discomfort of testing altogether.

Blood constituent monitoring is particularly important in the context of diabetes, a metabolism disorder affecting millions of people. Blood sugar (glucose) levels are directly indicative of the diabetic condition. Testing of blood glucose levels has for many years been performed invasively by taking a blood sample and externally determining the glucose level, generally by chemical reaction followed by colorimetric comparative testing.

A recent advance in noninvasive testing is described and claimed in U.S. Pat. No. 5,139,023 to Stanley et al. The patent teaching deals with monitoring blood glucose caused to permeate through a mucose or epithelial membrane. A number of examplary tests are listed in the patent in which glucose is collected in a sample collector and thereafter tested with conventional techniques.

SUMMARY OF THE INVENTION

It is accordingly an object of the invention to provide an integrated system for biological fluid constituent analysis, which overcomes the hereinafore-mentioned disadvantages of the heretofore-known devices of this general type and which provides for sample collection and testing in the form of a simple, easy-to-use, integrated system. Another object of the invention is to improve the accuracy of the test results as compared to the prior art, and to disband with the necessity of repetitive testing and the inconvenience and discomfort of testing.

With the foregoing and other objects in view there is provided, in accordance with the invention, an integrated system for biological fluid constituent analysis, comprising:

collector means for non-invasively collecting a body fluid analyte from a patient and indicator means responsive to the body fluid analyte for indicating a condition of the body fluid analyte;

electronic interpretation means receiving the indicator means and electro-optically interpreting the indicator means with regard to the condition of the body fluid analyte.

In a preferred embodiment, the body fluid is a transdermally excreted body fluid.

In accordance with an added feature of the invention, the collector means are in the form of a multi-layer laminate including a chemical reactant layer coated with a test reagent and color developer specifically provided for a given test, an activation gel layer disposed below the chemical reactant layer, a collection gel layer disposed below the activation gel layer, and a skin interface membrane layer disposed below the collection gel layer for placement on the patient's skin.

In accordance with another feature of the invention, the activation gel layer is a hygroscopic biopolymer gel with a biochemical intermediate incorporated therein for reacting with the collected body fluid analyte and producing a specific by-product in the reaction for detection in the chemical reactant layer. The biochemical intermediate is preferably an enzyme.

In accordance with an added feature of the invention, the collection gel layer includes a hygroscopic biopolymer gel with an osmotic flow enhancer incorporated therein and specifically selected for the body fluid analyte to be tested.

In accordance with a further feature of the invention, the indicator means are in the form of a color wheel, the color wheel being divided into a plurality of color segments each communicating with the chemical reactant layer for displaying a given color in response to a given amount of body fluid analyte processed through the layers.

In accordance with again a further feature of the invention, the electronic interpretation means include a light source for illuminating the indicator means received therein, a photosensor sensing a reflection intensity from the indicator means, and means for interpreting the measured reflection intensity and providing information regarding a result of the interpretation.

With the above-listed and objects in view, there is also provided, in accordance with yet another feature of the invention, a collection and indication apparatus for biological fluid constituent analysis, which comprises collector means for non-invasively collecting a body fluid analyte from a patient in the form of a multi-layer laminate including a chemical reactant layer, an activation gel layer disposed below the chemical reactant layer, a collection gel layer disposed below the activation gel layer, and a skin interface membrane layer disposed below the collection gel layer for placement on a patient's skin; and indicator means responsive to the body fluid analyte for indicating a condition of the body fluid analyte. Preferably, the body fluid is collected transdermally.

In other words, the system of the invention includes three major operational components. The first is the test patch which functions as the collection and analysis component, the second is the mechanical holder/reader which enables the health care professional to review the data in a rapid and meaningful way, and thirdly the electronic interpretation component. The latter component of the system is configured so as to read the "patch" component in the event of a visual impairment, or if a more precise numerical value is required and it will give the report in that format.

The novel method of combining test chemistries known to those in the healing arts with the interstitial fluid collection medium in such a manner as to cause to be absorbed through the skin a quantity of body fluid sufficient for the chemical test to proceed and then to have the ability to read and record the results in a very short time. This is one of the major objects of this invention.

An integral component of the invention is the patch which allows the system to work as a non-invasive skin test for clinical analytes. Additionally what is shown and described is the holder/reader and the electronic interpreter. All of which work together as a new and novel system to evaluate chemical analytes from non-invasivly obtained biological fluids.

Other features which are considered as characteristic for the invention are set forth in the appended claims.

Although the invention is illustrated and described herein as embodied in an integrated system for biological fluid constituent analysis, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

BRIEF DESCRIPTION OF THE DRAWINGS

FIG. 1b is a cross-sectional view of the device taken along the line I—I of FIG. 1a;

FIG. 2b is a cross-sectional view taken along the line II—II of FIG. 2a;

FIG. 3 is an enlarged view of a detail of FIG. 1b showing the multilayer composite construction;

FIG. 5b is a perspective view of the reader of FIG. 5a;

DESCRIPTION OF THE PREFERRED EMBODIMENTS

Figure 1A:
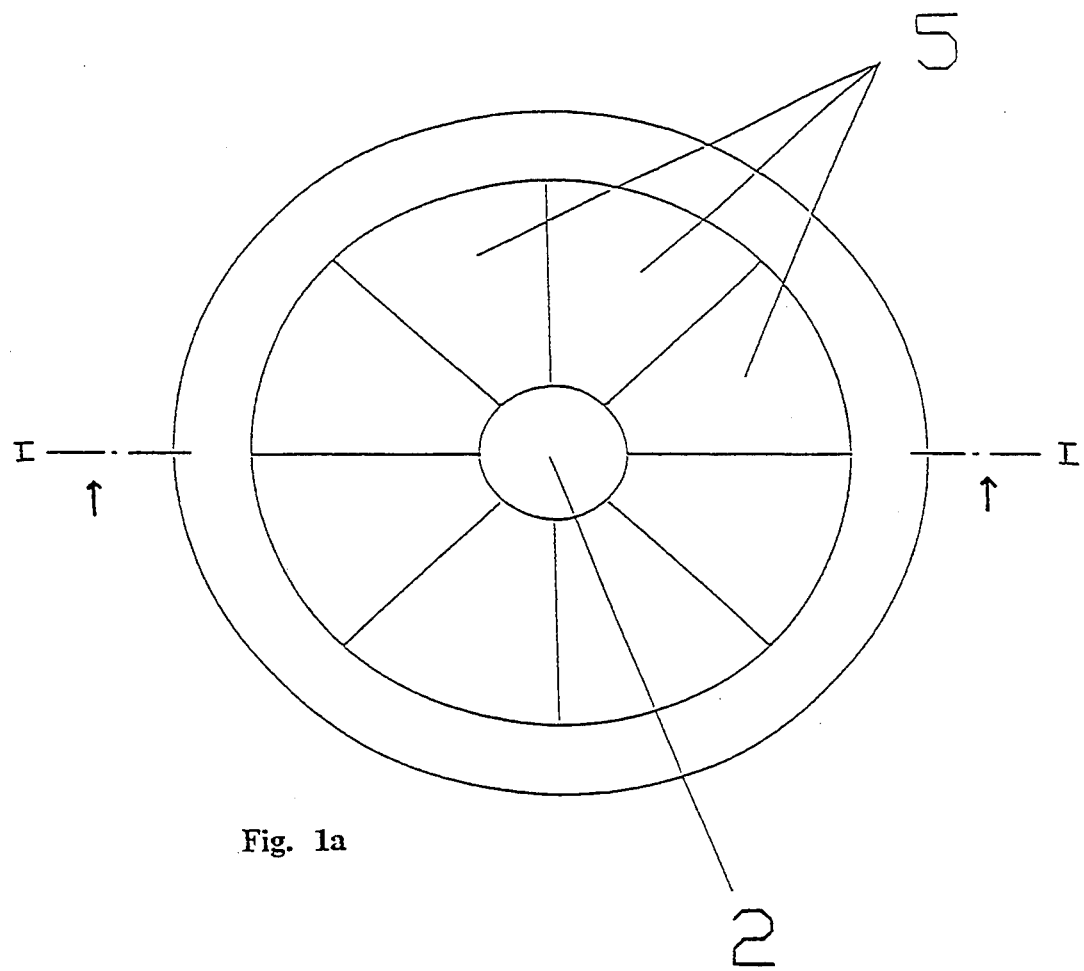
FIG. 1a is a bottom-plan, diagrammatic view of a collector patch with a color wheel according to the invention.
Figure 1B:
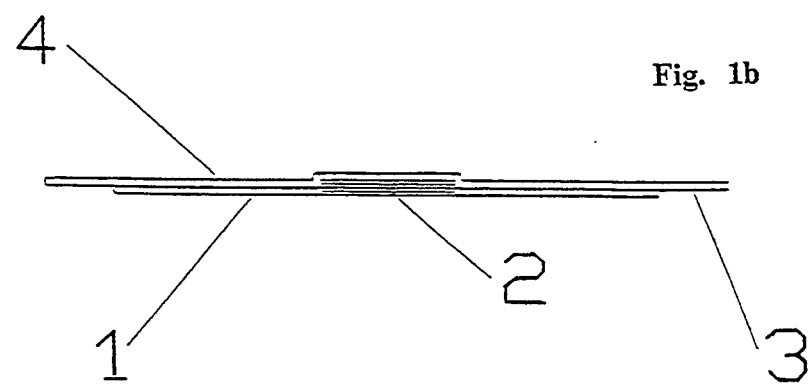

Referring now to the figures of the drawing in detail and first, particularly, to FIGS. 1a and 1b thereof, there is seen a collector/test patch of a multi-layer composite construction. The patch includes an occlusive backing 4 on the dorsal side of the device. The backing 4 functions as the support as well as the upper-outer protective layer to which a color wheel 1 is affixed. A center of the color wheel is punched out to allow the insertion of active collection components 2 or test/collection components 2 to be centered within the color wheel 1. The function of the color wheel 1 is to provide a visualization of the test reaction based on the differential colorometric chemistry employed for a given analyte. Accordingly, the color wheel 1 may be referred to as indicator means. The active collection components 2 may be referred to as the collector means. Coated on the perimeter of the backing and marginally to the color wheel is an adhesive layer 3 which allows the device to be placed on the skin and remain in contact with the skin during the required time period.

With reference to FIG. 3, the test reaction and collection area 2 is comprised of several layers 7–10 which form a central part of the system. Each layer has a specified function. Layer 10 is a chemical reactant layer that is coated with the specific test reagents and color developer required for any given test. Layer 9 is an activation gel layer that is made up of a selected hygroscopic biopolymer gel into which there is incorporated a biochemical intermediate such as an enzyme which will react with the collected sample to produce a very specific by-product to be detected by the test layer reagent. Layer 8 is a collection gel layer and includes the selected hygroscopic biopolymer gel incorporating an osmotic flow enhancer selected for the analyte of interest.

Osmotic flow enhancers are well known to those skilled in the art. They include distilled water, ionized water, ethanol, DMSO and other similar compounds. Layer 7 is a rate controlling membrane and skin interface membrane. The function of the layer 7 is to provide a constant flow of interstitial or other fluid into the collection gel 8 under the influence of the osmotic flow enhancer. Individual area segments 5 of the color wheel 1 are pie-shaped color definition segments that are used to evaluate the test results from the color developed in the test/collection area 2.

Figure 2A:
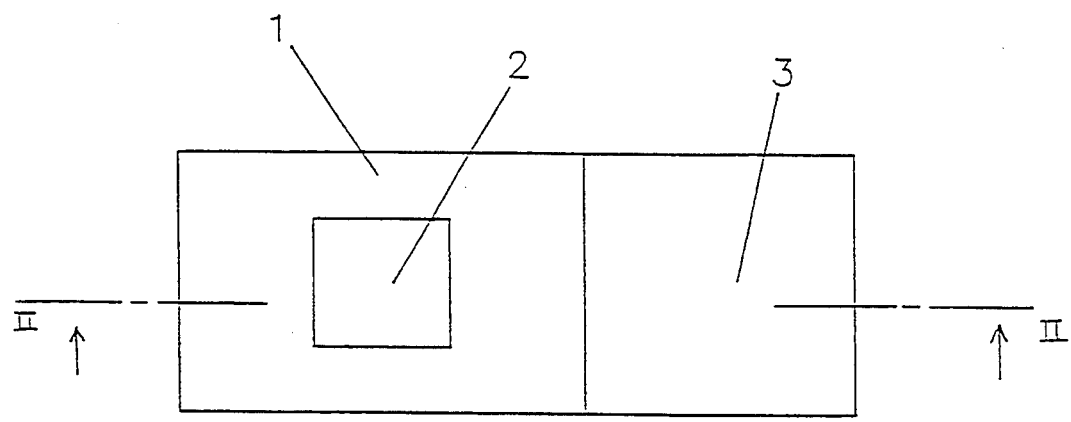
FIG. 2a is a top-plan view of a strip-type embodiment of the collector/test patch.
Figure 2B:
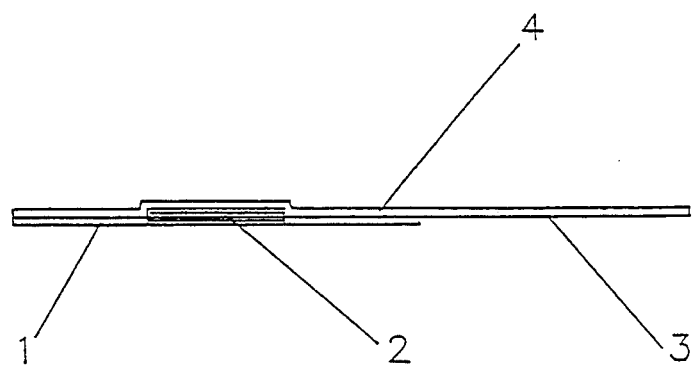

The strip of FIGS. 2a and 2b constitutes a further embodiment of the inventive collection patch. Instead of the round configuration, the device provided in the form of a more traditional shape "bandage" and the colors are displayed around the perimeter of the square test/collection well 2. This shape is more suitable for certain parts of the body or for use on some animal species other than man. This design incorporates the adhesive into the area of 1 the color display and leaves the area 3 free of skin contact adhesive to simplify the removal and handling of the device.

Figure 4A:
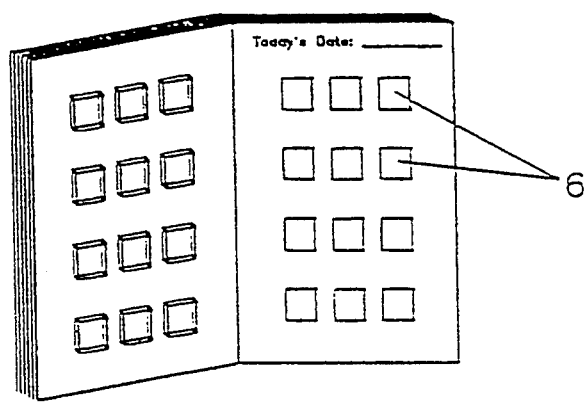
FIG. 4a and 4b are perspective views of two exemplary holder/reader booklets for use in the system.
Figure 4B:
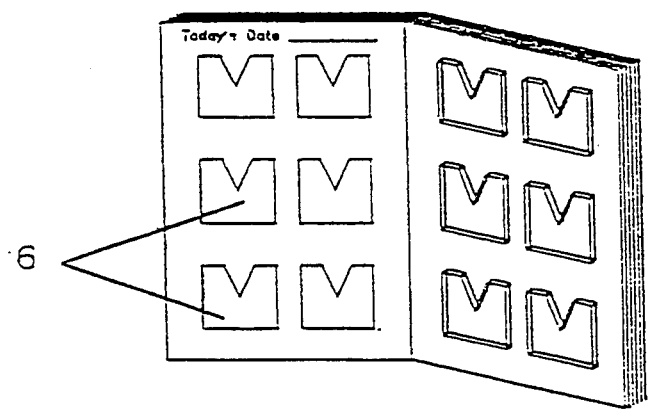

Referring now to FIG. 4, a holder/reader device is in the form of a booklet which incorporates a clear area for visualization of the results and the placement of the test/collector in such a manner that only the result segment or sector is visible. In other words, the person taking the tests places the color wheel or the indicator portion of the square patch into pouches 6 of the booklet in a certain way. Thus the health professional responsible for the final interpretation of the test can quickly scan the daily sheets and pick out the trends or tendencies for the particular test. The construction of the holder/reader is such that a usual daily number of tests can be displayed on a given page. The holder also allows for the user to to be reminded about the performance of the tests at a given time by the sequencing of the holders and a space to write comments or other pertinent information regarding the test performed.

Figure 5A:
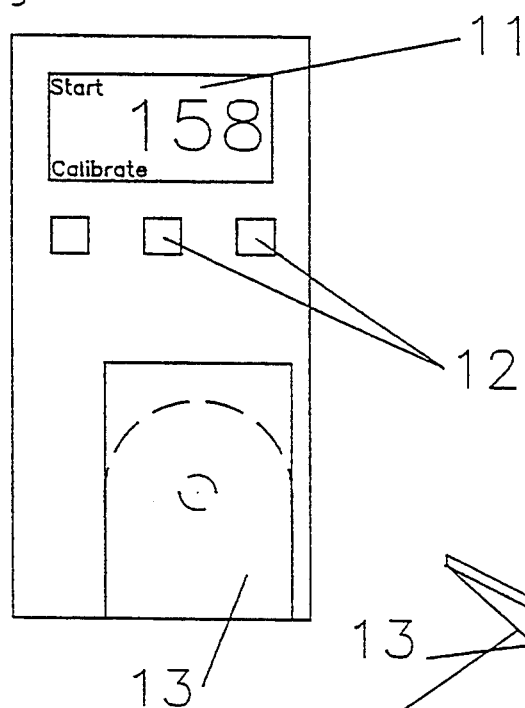
FIG. 5a is a top-plan view of an electronic reader according to the invention.
Figure 5B:
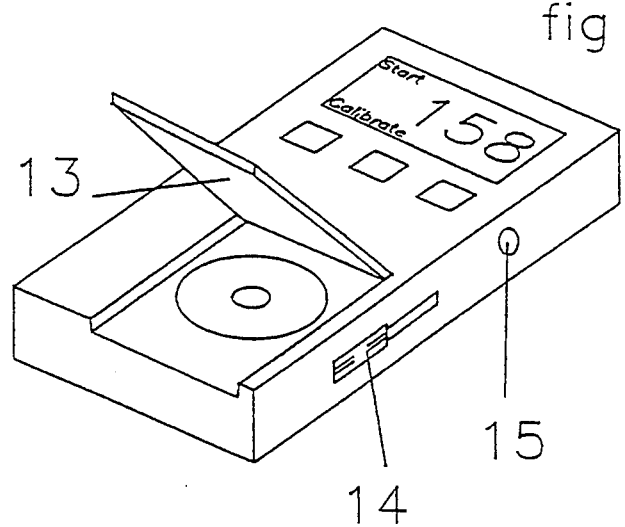

Referring now to FIGS. 5a and 5b, an electronic reader and interpretation device can be programmed to give specific diagnostic information based on the results of a reading of the test/collector device. The "patches" or "bandaids" can be read directly by the device as an aid to the visually impaired or to remove "operator" error. Additionally, information regarding daily sequential readouts may be stored for later summary display or interface transmission to a host computer.

The round patch is placed in a compartment 13, where it is read when the lid is closed. A slot 14 is provided for the insertion of the bandaid strip, again for reading the color information and displaying and/or storing the result. A connector 15 is provided for interfacing the device with a modem and/or a host computer to transmit the stored data to a remote diagnostic facility of a doctor's office, for instance. Control buttons 12 are used to change the mode, start and stop, and calibrate the device as required. A display 11 is in the form of an LED alphanumeric display or an LCD (liquid crystal display) which gives all the required operator instructions and results in accordance with program instructions.

Figure 6:
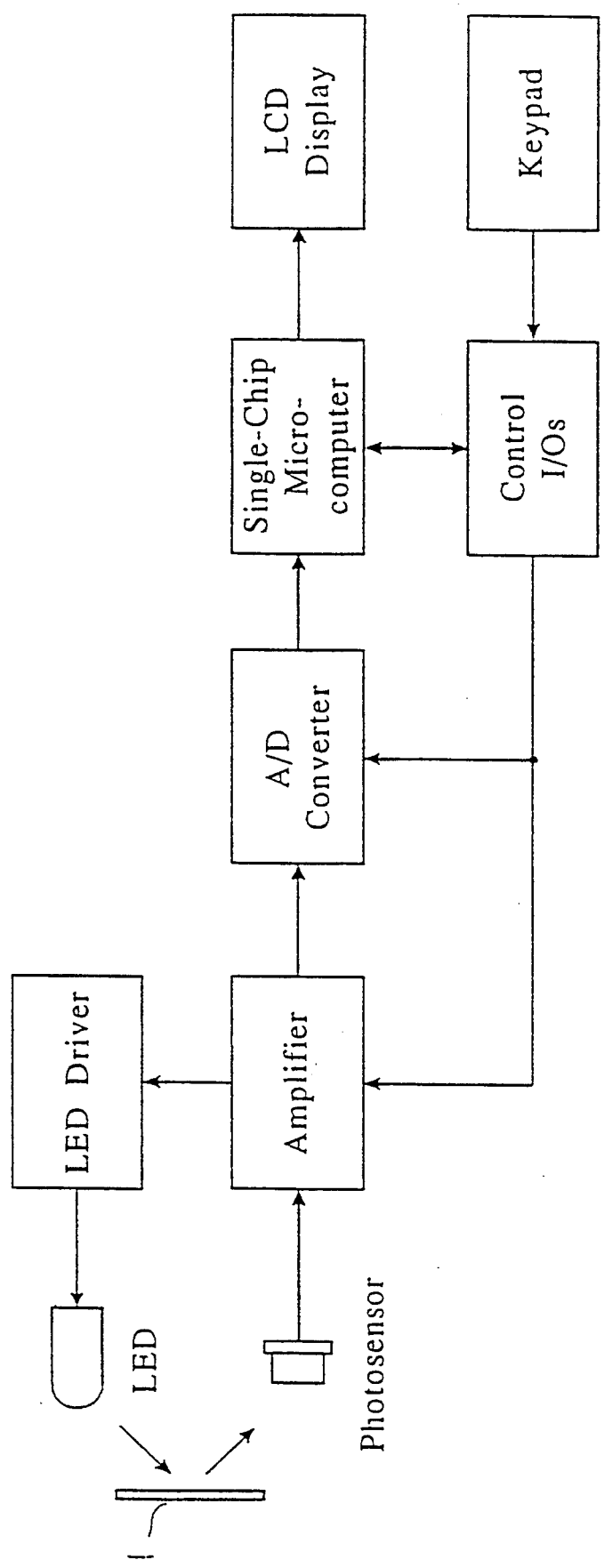
FIG. 6 is a diagrammatic circuit layout for the electronic system reader.

With reference to FIG. 6, in which the individual components of the electronic reader device are labeled, the patch 1 (for instance the color wheel) is exposed to a light source, for instance an infrared light emitting diode or LED (e.g. Omron EE-SY124). A photosensor picks up the reflected optical wavelength (e.g. Omron EE-SY124). A light source driver is provided for the purpose of establishing a constant current source for the LED, so as to obtain a stable light output for the measurement. A photosensor amplifier converts the photosensor output signal into a voltage signal in a range which is appropriate for the following analog to digital (A/D) conversion. An A/D converter connected downstream converts the voltage signal which is proportional to the intensity of reflectance to a digital signal for further processing (e.g. National Semiconductor ADC 0804). The digital information is transmitted to a single-chip microcomputer (e.g. Intel 8051 series). The microcomputer includes a read only memory segment (ROM), a random access memory segment (RAM), input and output terminals (I/O ports), an internal timer and a central processing unit (CPU). The microcomputer thus provides all of the necessary signal processing, process control, keypad interpretation, display, clocking and timing functions. An LCD segment displays information for the operator in the form of text and graphics (Epson EA-D16015). An I/O interface is the required circuit for I/O operations and, finally, a keypad allows the operator to enter certain information.

Figure 7:
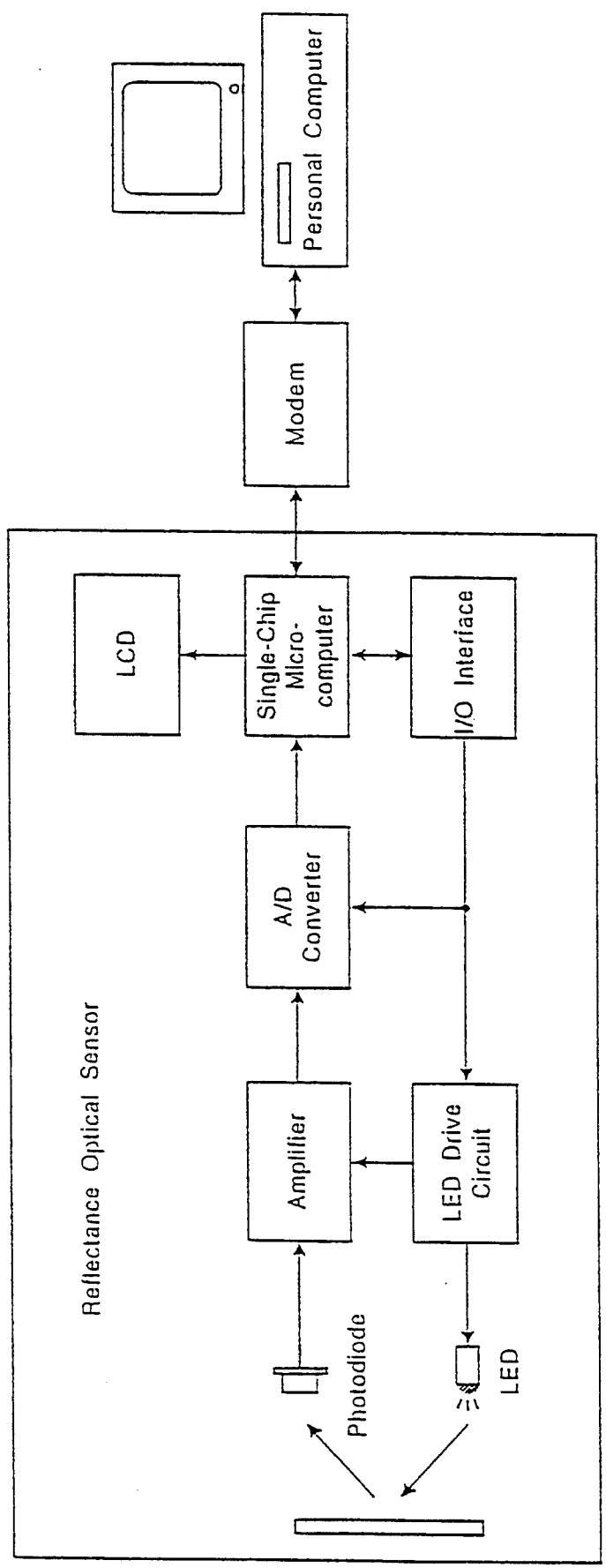
FIG. 7 is a diagrammatic view of the optical reader system in interface communication with a computing device.

FIG. 7 illustrates the circuit of FIG. 6 as it is in communication with a host computer, preferably a PC.

Figure 8:
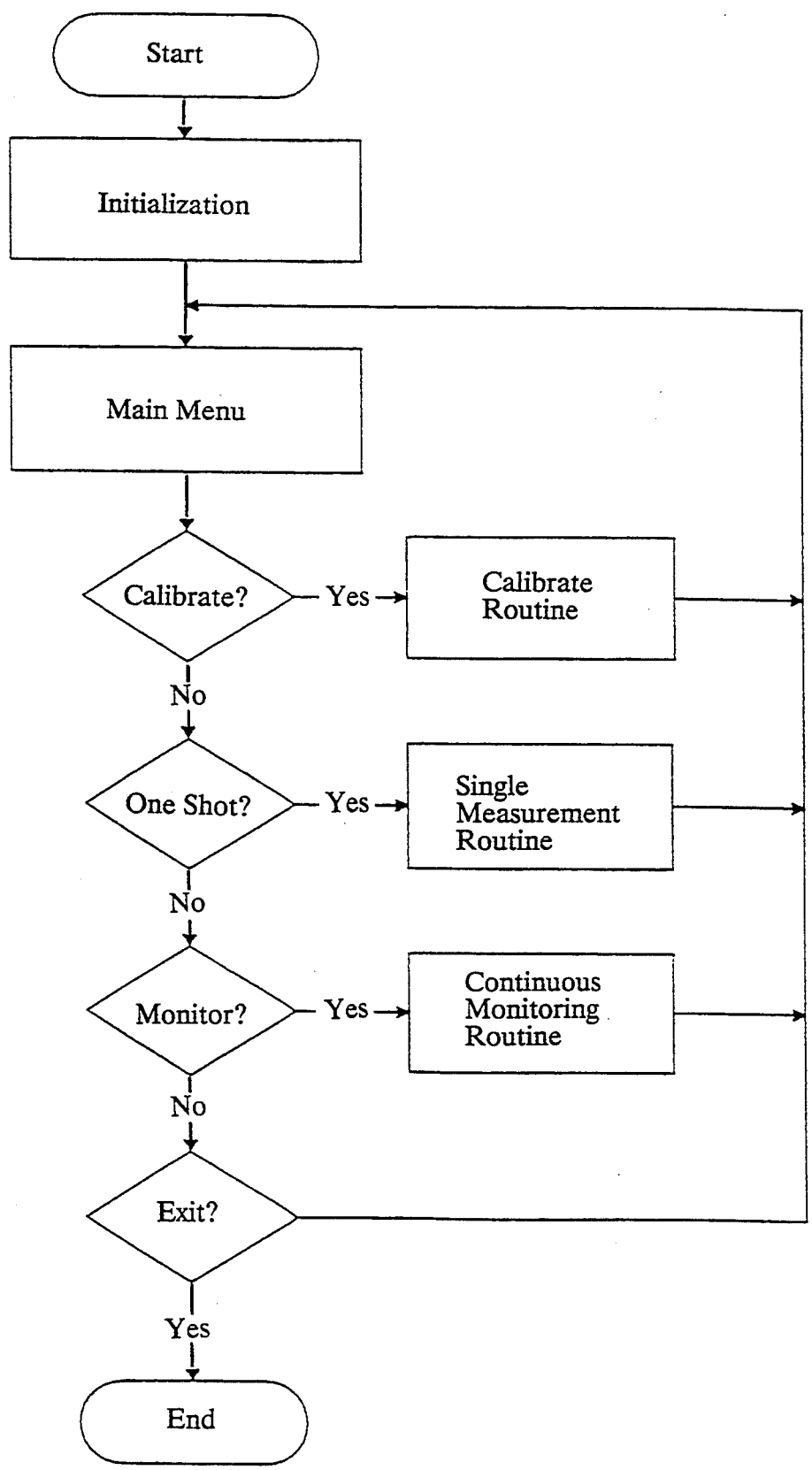
FIG. 8 is a flow chart illustrating a main operating program of the optical reader.

With reference to FIG. 8, the program start may be triggered by a start button or automatically upon the closing of the lid 13 or the insertion of the patch in the slot 14. After an initialization routine, the program moves to the main menu. If the device has not been calibrated for some time, or it is the first measurement in a series of tests, the program branches to a calibration routine. After calibration the program inquires whether the measurement is to employ a single shot measurement run, or if the sample is to be continuously monitored.

Examples:

A non-invasive glucose collector/test patch was tested in a first example. A peroxide test strip (EM Science, Div. of E. Merck Co.) active area was coated with a polymer gel containing 50 units of peroxidase reagent (Sigma Chemical Co.) and 150 units of glucose oxidase enzyme (Sigma Chemical Co.). The coated test strip was then allowed to dry. Subsequently, the test area was coated with a flow enhancer comprising a gelled ethyl alcohol/water mixture. The coated test area was then placed onto the test patch and covered with a support membrane. The test patch was then placed on exposed skin behind the ear of a human patient. After 45 minutes, the patch was removed from the patient and it indicated the transudate glucose level.

In a second example, the preparation was similar to that of the first example, except that the flow enhancer gel and the reaction gel were mixed together in equal proportions and then applied to the underlying test area prior to use. Results were clearly seen after 30 minutes.

In each of the examples, the indicators of the patches were also subjected to an electronic measurement of the glucose level indication. The electronic system provided exact numerical readouts of the patients' glucose levels.

Figure 9:
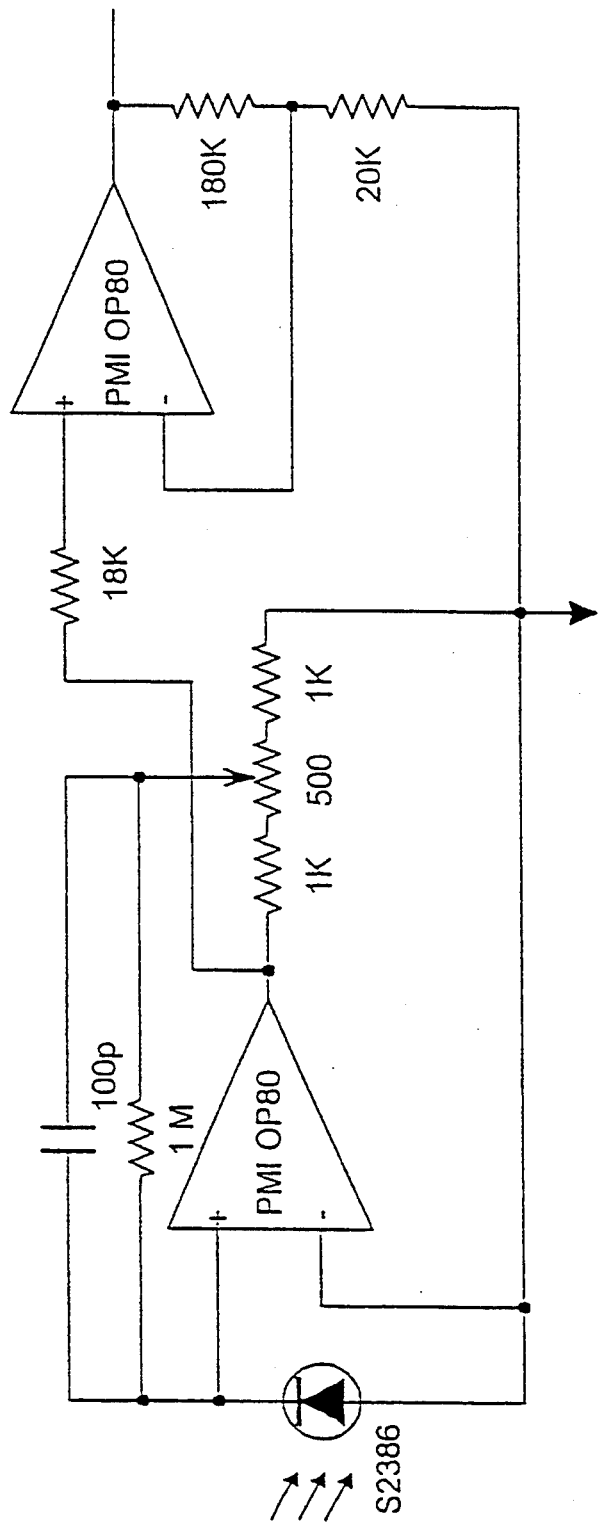
FIG. 9 is a diagram of an optimized photodiode amplifier circuit.
Figure 10:
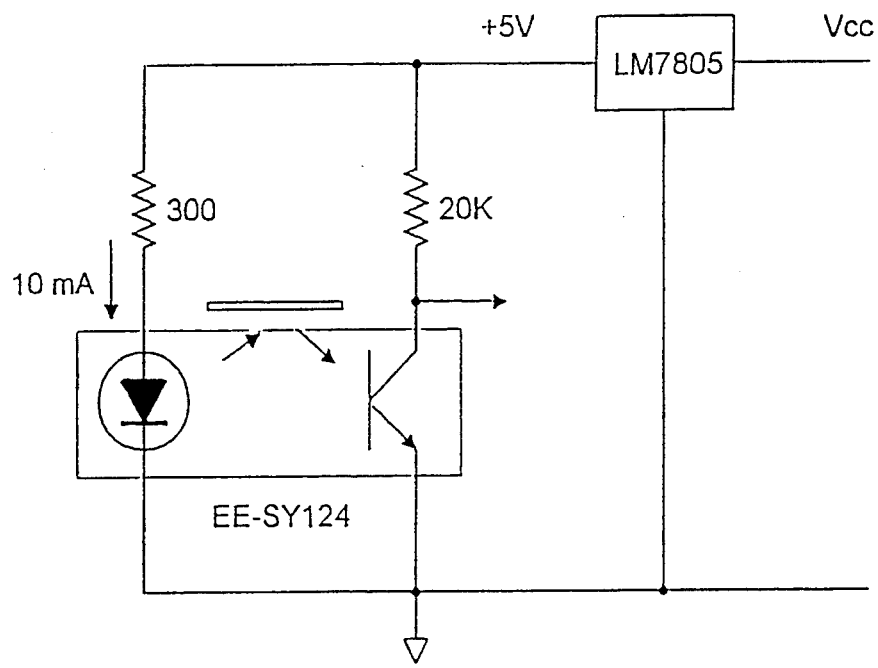
FIG. 10 is a diagram of an optimized light source and photo sensor circuit.
Figure 11:
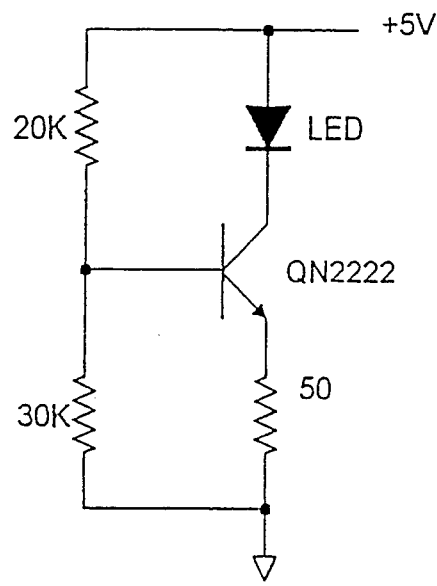
FIG. 11 is a diagram of an optimized LED driver.

Optimized subcomponent circuits of the electronic device are illustrated in FIGS. 9–11, with values indicated for the discrete components and model numbers for the integrated circuits.

We claim:

1. An integrated system for biological fluid constituent analysis, comprising:

collector means for non-invasively collecting a body fluid analyte from a patient and indicator means responsive to the body fluid analyte for indicating a condition of the body fluid analyte;

electronic interpretation means receiving said indicator means and electro-optically interpreting said indicator means with regard to the condition of the body fluid analyte;

wherein said collector means are in the form of a multi-layer laminate including a chemical reactant layer coated with a test reagent and color developer specifically provided for a given test, an activation gel layer disposed below said chemical reactant layer, a collection gel layer disposed below said activation gel layer, and a skin interface membrane layer disposed below said collection gel layer for placement on the patient's skin; said indicator means being in the form of a color wheel, said color wheel being divided into a plurality of color segments each communicating with said multi-layer laminate for displaying a given color in response to a given amount of body fluid analyte processed through said layers.

2. The system according to claim 1, wherein said activation gel layer is a hygroscopic biopolymer gel with a biochemical intermediate incorporated therein for reacting with the collected body fluid analyte and producing a specific by-product in the reaction for detection in said chemical reactant layer.

3. The system according to claim 1, wherein said collection gel layer includes a hygroscopic biopolymer gel with an osmotic flow enhancer incorporated therein and specifically selected for the body fluid analyte to be tested.

4. The system according to claim 1, wherein said electronic interpretation means include a light source for illuminating the indicator means received therein, a photosensor sensing a reflection intensity from the indicator means, and means for interpreting the measured reflection intensity and providing information regarding a result of the interpretation.

5. The system according to claim 1, wherein said collector means for collecting a body fluid analyte are means for collecting a transdermally excreted body fluid analyte.

6. A collection and indication apparatus for biological fluid constituent analysis, comprising:

collector means for non-invasively collecting a body fluid analyte from a patient in the form of a multi-layer laminate including a chemical reactant layer, an activation gel layer disposed below said chemical reactant layer, and a collection gel layer disposed below said activation gel layer; and indicator means contiguous with said collector means and responsive to the body fluid analyte for indicating a condition of the body fluid analyte, said indicator means being in the form of a color wheel, said color wheel being divided into a plurality of color segments each communicating with said multi-layer laminate for displaying a given color in response to a given amount of body fluid analyte processed through said layers.

7. The apparatus according to claim 6, including a skin interface membrane layer disposed below said collection gel layer for placement on a patient's skin.

8. The apparatus according to claim 6, wherein said chemical reactant layer is coated with a test reagent and color developer specifically provided for a given test.

9. The apparatus according to claim 6, wherein said activation gel layer is a hygroscopic biopolymer gel with a biochemical intermediate incorporated therein for reacting with the collected body fluid analyte and producing a specific by-product in the reaction for detection in said chemical reactant layer.

10. The apparatus according to claim 8, wherein said biochemical intermediate incorporated in said hygroscopic biopolymer gel is an enzyme.

11. The apparatus according to claim 7, wherein said collection gel layer includes a hygroscopic biopolymer gel with an osmotic flow enhancer incorporated therein and specifically selected for the body fluid analyte to be tested.

12. The apparatus according to claim 6, further including storage means in the form of a booklet having pouches formed therein for receiving a plurality of said indicator means and for displaying indications of various test results.

* * * * *

UNITED STATES PATENT AND TRADEMARK OFFICE
CERTIFICATE OF CORRECTION

PATENT NO. : 5,443,080
DATED : August 22, 1995
INVENTOR(S) : Joseph P. D'Angelo, et al.

It is certified that error appears in the above-indentified patent and that said Letters Patent is hereby corrected as shown below:

On the title page, item [73]: Change the Assignee to

-- Americare Transtech, Inc. --.

Signed and Sealed this

Twenty-sixth Day of December, 1995

Attest:

BRUCE LEHMAN

Attesting Officer        Commissioner of Patents and Trademarks